(12) United States Patent
Kacian et al.

(10) Patent No.: US 6,610,475 B1
(45) Date of Patent: Aug. 26, 2003

(54) KITS FOR PROCESSING BIOLOGICAL SPECIMENS FOR NUCLEIC ACID HYBRIDIZATION ASSAYS, TARGET AMPLIFICATION REACTIONS AND SIMILAR USES

(75) Inventors: Daniel L. Kacian, San Diego, CA (US); Kiyotada Nunomura, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 08/347,272

(22) Filed: Nov. 30, 1994

Related U.S. Application Data

(62) Division of application No. 08/015,729, filed on Feb. 10, 1993, now Pat. No. 5,386,024.

(51) Int. Cl.[7] .............................. C12Q 1/68; C12N 9/22; C12N 9/50
(52) U.S. Cl. .............................. 435/6; 435/5; 435/183; 435/184; 435/195; 435/199; 435/219; 435/810
(58) Field of Search ................. 435/6, 5, 183, 435/184, 195, 199, 219, 810; 436/174, 175; 536/24.3, 24.32, 25.4; 935/77, 78

(56) References Cited

U.S. PATENT DOCUMENTS 4,900,677 A   2/1990   Hewitt ..................... 435/259

FOREIGN PATENT DOCUMENTS

| EP | 0261956 | 3/1988 |
| WO | 9010715 | 9/1990 |
| WO | 9102740 | 3/1991 |
| WO | 9208807 | 5/1992 |

OTHER PUBLICATIONS

Chen et al. The Journal of Biological Chemistry. 1991. 266: 11718–11725.*
Hashimoto et al. Applied Microbiology. 1973: 584–588.*
Sambrook et al, Molecular Cloning: A Laboratory Manual, 2$^{nd}$Ed, Cold Spring Harbor, Laboratory Press, ColdSpring Harbor, NY., (1989), B. 16.*
Tecott et al, In Situ Hybridization: Applications to Neurobiology, Valentino et al, Eds., 1987, Oxford University Press, N.Y. N.Y. pp. 1–24.*
Stratagene Catalog (1988) p 39.*
Amortegui et al, Clinical Biochemistry (1990) 23: 301–306.*
Arrand, "Preparation of Nucleic Acid Probes," in *Nucleic and Hybridisation—A Practical Approach*, pp. 17–20, Hames and Higgins eds., IRL Press, Oxford (1985).
*Calbiochem 1992 Catalog*, p. 236 (1992).
Naoumov et al., "In Situ Hybridisation in Formalin Fixed, Paraffin Wax Embedded Liver Specimens: Method for Detecting Human and Viral DNA Using Biotinylated Probes," *J. Clin. Pathology* 41:793–798 (1988).

* cited by examiner

*Primary Examiner*—Carla J. Myers
(74) *Attorney, Agent, or Firm*—Charles B. Cappellari; Sheldon O. Heber

(57) ABSTRACT

The present invention features kits for making available a desired nucleic acid contained in a biological sample. The kits contain an acid for acidifying the biological sample to a pH at which endogenous nucleases capable of degrading desired nucleic acids are inactive and an acid protease able to digest cellular materials in the biological sample to release nucleic acid and to inactivate endogenous nucleases which may be present.

5 Claims, No Drawings

KITS FOR PROCESSING BIOLOGICAL SPECIMENS FOR NUCLEIC ACID HYBRIDIZATION ASSAYS, TARGET AMPLIFICATION REACTIONS AND SIMILAR USES

This is a division of application Ser. No. 08/015,729, filed Feb. 10, 1993, now U.S. Pat. No. 5,386,024.

FIELD OF THE INVENTION

The present invention relates to procedures for treating biological specimens to make their nucleic acids available for various purposes, such as nucleic acid hybridization assays for the diagnosis of disease and other purposes, and for amplification of nucleic acids by the polymerase chain reaction (PCR) or other target amplification procedures. Specifically, the present invention relates to convenient procedures for making nucleic acids available that prevent degradation of the nucleic acids by endogenous nucleases present in the biological sample.

BACKGROUND OF THE INVENTION

Many diagnostic procedures are based on detection of specific nucleic acid (DNA or RNA) sequences present in a biological sample. For example, the sample may contain bacteria, viruses, or other microorganisms whose presence must be ascertained to determine the cause of an infectious disease. In other instances, the nucleic acid sequence may be sought within the DNA of a human white blood cell in order to establish the presence of a mutation associated with cancer or a genetic disease.

For such a diagnostic analyses, it is necessary to make available the specific nucleic acid that may be present in the sample. Frequently, the nucleic acid will be contained within a bacterium, fungus, virus, or other microorganism or within human cells such as white blood cells. It may further be contained within other structures such as ribosomes, plasmids, or chromosomal DNA. In order to perform hybridization reactions to detect specific nucleic acids or to amplify them using PCR or other target amplification methods, the nucleic acid must be released from these organisms and/or structures.

Unfortunately, such release exposes the nucleic acids to degradation by endogenous nucleases present in the sample, which may exist in such abundance that the nucleic acid is almost instantaneously destroyed.

The problem is particularly acute when the specific nucleic acid is an RNA, since RNAses are abundant in most biological samples and are often extremely resistant to treatments that readily inactivate many other enzymes.

To deal with this problem, it is common in the art to employ a variety of means to purify the nucleic acids from the biological sample. For example, anionic detergents and chaotropic agents such as guanidinium salts have been used to simultaneously inactivate or inhibit nuclease activities and release nucleic acids from within cells and subcellular structures. Unfortunately, these agents are also potent inhibitors of the enzymes used in target amplification processes or in many hybridization detection methods or, in the case of chaotropes, may interfere with hybridization itself. Therefore, it has been necessary to use additional steps to remove these agents and recover the nucleic acids.

The most commonly used procedure is to precipitate the nucleic acids from the sample using various salts and ethanol. The sample must be kept at reduced temperature (usually −20° C. or lower) for some hours and centrifuged at high speed in order to achieve good yields of nucleic acids in most instances.

Because other macromolecules also precipitate under these conditions producing a sticky, intractable mass that entraps the nucleic acids, it has been frequently necessary to resort to extraction of the sample with hazardous organic solvent mixtures containing phenol, cresol, and/or chloroform prior to ethanol precipitation. In some cases when anionic detergents are used, proteases that are active in the presence of these detergents, such as proteinase K or pronase, are used to partially degrade protein components of the sample to minimize entrapment during organic solvent extraction, and/or degrade components that may not be extracted by the solvent treatment.

It will be readily appreciated that these methods are complex, tedious, labor-intensive, and slow. If great care is not taken in performing the procedure, residual contamination with nucleases can occur, and the sample nucleic acids will be degraded or lost. Diagnostic tests performed with such samples may give false negative results. False negative results can also be obtained if residual anionic detergents, chaotropic salts, or ethanol remain in the sample and inhibit hybridization and/or target amplification procedures. If anionic detergents and proteases have been used, residual proteolytic activity can also degrade the enzymes used in target amplification and/hybridization detection reactions and produce false negative results. On the other hand, improper processing with these methods can also result in the isolation of denatured proteins or other macromolecules that can entrap labelled probes and produce false positive results with diagnostic tests involving nucleic acid hybridization. Thus, these procedures are not well suited for routine processing of biological specimens received in clinical laboratories in any quantity.

Particularly, trouble is encountered with many biological samples in which the desired nucleic acid species is RNA, and the sample contains significant amounts of RNAse of the "pancreatic" type (also frequently referred to as "ribonuclease A"). Pancreatic RNAses are present in serum and plasma and in many tissues of the body. They are resistant to denaturation by heat and acids and will even withstand boiling in 1 N HCl for 10 minutes without loss of activity. They are inhibited by anionic detergents, chaotropes, and organic solvents such as phenol, but are not irreversibly inactivated by these agents; therefore, when the detergents, chaotropes, or solvents are removed, the RNAse (if not eliminated by careful extraction) can proceed to degrade the desired RNA.

Exposure to strong alkali will irreversibly inactive these RNAses; however, such conditions also result in the degradation of RNA itself.

The present invention addresses these problems by providing a method for conveniently inhibiting and inactivating nucleases in biological samples while making available sample nucleic acids for hybridization assays, target amplification procedures, or other uses. Inhibitory detergents or chaotropes are not required in the sample, and there is no residual proteolytic activity. The method is simple and applicable to processing large numbers of samples simultaneously. Unlike ethanol precipitation methods, it does not use hazardous organic solvents, nor require equipment for cooling the sample or recovering precipitates by centrifugation.

SUMMARY OF THE INVENTION

The present invention features a procedure for irreversibly inactivating endogenous nucleases in biological samples by reducing the pH below that at which the endogenous nucleases present in the sample are active, adding a protease which is active at that pH and which degrades any nucleases that have not been irreversibly inactivated by exposure to low pH, and then inactivating the protease (after it has done its work) by raising the pH. At the higher pH, the chosen protease is either inactive or is irreversibly inactivated. If possible, the protease is chosen so as to aid in the digestion of other macromolecules in the sample that may interfere with the intended use of the sample, and chosen to help make available the desired nucleic acids by degrading microorganism cell walls, virus particles, ribosomes, and/or other structures containing the desired nucleic acids. Alternatively, solubilization of these structures and release of the nucleic acids may be effected by the use of detergents, heat, or other means once sample nuclease activity has been effectively controlled, reduced, or eliminated.

In general, the biological sample is adjusted to a low pH where the endogenous nucleases are either irreversibly inactivated or are effectively inhibited. Exogenous acid protease (such as pepsin) is then added or may be added simultaneously with the pH lowering solution. The action of the acid protease digests the endogenous nucleases present in the sample and irreversibly inactivates them so that they will not degrade the sample nucleic acids when the pH is subsequently raised. In addition, the protease will usually act to liberate the nucleic acids from microorganisms, human cells, or subcellular components such as ribosomes and nuclei. It will also degrade many protein components of the biological sample, including ones that may interfere with subsequent use of the sample for hybridization assays and/or target amplification procedures.

The acid protease selected should have activity at an acidic pH, pH 1.0 to pH 4.0, and be able to digest a wide variety of proteins, including the nucleases found in the sample as well as other unwanted components. In addition, it should ideally be able to digest components which contain the desired nucleic acid. In some cases, it may be desirable to select a protease of more limited specificity in order that a nucleic acid (whose presence in free form in the sample is undesirable) is not liberated from its component structures.

The acid protease should also be checked to ensure that it is itself free of nuclease activities that are active at the chosen acidic pH or which are resistant to degradation and inactivation by the chosen acidic protease.

Commercial preparations of acid proteases may be contaminated with such enzymes and should be purified, if necessary, to eliminate them. In the examples that follow, a procedure for purifying commercially available pepsin preparations to eliminate residual RNAse activities that are not eliminated by pepsin digestion is given. Equivalent procedures can be used for other proteases.

The protease is rendered inactive by the simple act of raising the pH. With some acid proteases, this is sufficient to completely stop further proteolytic digestions and may irreversibly denature and inactivate the enzyme. With other proteases, it may be necessary to resort to heating the sample to achieve complete inactivation of the protease. Since the nucleases have been destroyed and nucleic acids are not damaged by brief exposure to heat at neutral pH, they will survive this procedure intact.

Accordingly, this invention provides a simple procedure to extract nucleic acids in vitro. This procedure can be used for processing many biological samples, including those containing viruses, such as hepatitis C virus, which presents particular difficulties because it is an RNA-containing virus which is difficult to open, the sample is serum or plasma which contains significant amounts of pancreatic-type RNAse activity, and the virus is often present in very low amounts which makes recovery of the nucleic acids by ethanol precipitation techniques difficult.

Thus, in a first aspect, the invention features a method for purifying or making available a nucleic acid from a biological sample by acidifying the biological sample to a pH at which endogenous nucleases (capable of degrading the desired nucleic acids) are less active, e.g., to a pH between 1.0 and 4.0; contacting the biological sample with an exogenous acid enzyme active at that pH; incubating the sample until endogenous nucleases have been degraded to insignificant levels (i.e., to a level where their effect on levels of nucleic acids in the sample is insignificant, e.g., at a level where less than 5% of the nucleic acids are degraded over a period of 60 minutes at 37° C. in a standard salt solution); and raising the pH of the biological sample with a base to a pH sufficient to render the exogenous protease less active, e.g., to a pH at which the protease is no longer active.

By "making available" is meant that the nucleic acid is accessible for later analyses, such as hybridization or amplification.

By "less active" is meant, with respect to endogenous nucleases, is less nuclease activity than prior to treatment (under the same conditions). By "less active" is meant, with respect to exogenous proteases, is less protease activity than prior to treatment. Preferably, the lower exogenous protease activity is insufficient to reduce the activity of enzymes used in later processes involving the isolated nucleic acids.

By "degraded" is meant that the activity of the nucleases is reduced to a level which will allow later experiments or manipulations of the isolated nucleic acids.

By "desired nucleic acid" is meant a nucleic acid that is obtained, possibly along with other nucleic acids by this invention, and can subsequently be specifically identified.

In preferred embodiments, a biological sample is chosen from tissue cells, blood components, and other human biological materials which may contain infectious disease agents; the biological sample consists of human white blood cells, cancer cells, or other cells which offer a convenient source of human cellular nucleic acid for genetic analysis, body fluids, secretions, or tissues; the acid protease is pepsin; the pH of the sample after incubating, preferably at pH 4 or lower in the presence of exogenous protease, is raised up to a level suitable for subsequent use, but below that level at which the exogenous protease is completely inhibited or inactivated; in the acidifying step the pH is adjusted to between 1.0 and 4.0; in the raising step the pH is adjusted to be greater than 6.0; following the raising step the sample is heated to aid inactivation of the acidic protease and/or other enzyme activities present in the sample; detergents are added to the sample to aid release of the desired nucleic acid from other sample components; and the time of the incubating is longer than necessary to reduce endogenous nuclease levels to insignificant levels, in order to effect lysis of sample components and/or degradation of other sample components.

In related aspects, the invention features a kit including components necessary to carry out the method of this invention, and a method for purifying pepsin from RNAses for use in this method. Such purification makes use of an RNAse adsorbent which does not adsorb proteases, e.g., Macaloid or bentonite. Macaloid is a natural clay mineral product that has the property of adsorbing RNAses to its surface. Bentonite is a similar material which is a colloidal native hydrated aluminum silicate clay consisting primarily of montmorillonite. Both can often be used interchangeably to remove RNAses from a variety of biological materials. Other more-or-less specific adsorbents could be used provided they adsorb the RNAses and not the desired protease.

DESCRIPTION OF THE PREFERRED EMBODIMENTS

The present invention provides a procedure for isolating nucleic acids from different types of biological samples under acidic conditions where the degradation of these nucleic acids is minimized. This process is particularly useful for obtaining nucleic acids from specimens where there is a risk of significant degradation of nucleic acids by endogenous nucleases. Nucleic acids which can be isolated by this procedure include naturally occurring nucleic acids and synthetic nucleic acids or oligonucleotides.

The biological samples containing the nucleic acids to be isolated include tissue cells, blood components, viruses, microorganisms, pathogenic organisms, and body fluids containing these various organisms.

An initial step of the procedure of the present invention is adjustment of the acidity of the biological specimen containing the desired nucleic acids to about pH 4 or lower. At this pH, nucleases which may be present in the biological sample are not active. KCl—HCl buffer, glycine-HCl buffer, acetic acid buffer and various other acidic buffer compositions having buffering activity in acidic conditions, can be used to reduce the pH of the specimen. Endogenous nucleases present in clinical samples do not work (i.e., have negligible enzymatic activity) at a sufficiently acidic pH, since this pH is far below their optimum range. For example, serum RNAse has its optimum pH at about 6.5. It has almost no activity at pH 3.0 or lower. Leukocyte RNAse has an optimum pH range from 6.0 to 6.5 and has virtually no enzymatic activity at pH 4.0 or lower. Therefore, the adjustment of acidity of the mixture to about pH 4 or lower will prevent the action of most known endogenous RNAses.

Similarly, serum deoxyribonuclease activity has its optimum pH at about 5.8 to 7.0, depending upon the type of divalent metal(s) present. It shows little activity below pH 5.0, regardless of metal ion present. Leukocyte DNAse has an optimum pH range from about 4.0 to about 5.0, and it is virtually inactive below pH 3.0. The exact pH ranges at which nucleases found in clinical samples are active will depend upon such variables as the type of buffer used to control the pH, metal ion requirements, if any, and temperature.

For use of the present invention, those skilled in the art know how to assay for activities that degrade one or more nucleic acids of interest, and can easily determine the appropriate pH, buffer, and temperature that is needed for a particular sample type. In particular, it may be important to lower the temperature and minimize the time of exposure to very low pH when it is desired to recover DNA, since depurination of the DNA can occur at low pH when higher temperatures and longer times are employed. However, it is an important feature of the present invention that some DNA depurination and chain breakage may occur and is useful in that it helps to break up gelatinous aggregations of DNA that are produced when some biological specimens (for example, white blood cell pellets) are lysed. Thus, the present invention can address this additional specimen processing problem as an added benefit of the method.

The next step (which can be performed simultaneously, or even before, the first step if desired) is addition of an acidic protease into the acidified biolohical samples. The endogenous nucleases in the reaction mixture are digested and irrversibly inactivated by this protease. In this step, the desired nucleic acids may also be liberated from the biological sample into the aqueous solution when the biological components, e.g., cell membranes, are also digested by the acidic protease. Pepsin is one example of an acidic protease which can be used in this step. Other proteases can be used as long as they retain enzymatic activities under acidic conditions that inactivate the unwanted nuclease activities present in the biological sample. Such proteases are readily identified by those in the art using standard procedures.

Nucleic acids released by the steps described above are stable because the aqueous solution no longer contains active nuclease (even after neutralization of the solution to inactivate the acidic protease by addition of alkali). Such neutralization provides physiological conditions suitable for subsequent enzymatic reactions, e.g., for nucleic acid amplification procedures such as PCR, and cDNA polymerization methods. Thus, the neutralized solution may be used directly in such procedures without further processing, e.g., without removal of strong anionic detergents or other harsh agents which may affect the activity of enzymes used in subsequent processes.

This procedure provides significant advantages over other nucleic acid isolation methods, since no process is required to remove guanidine isothiocyanate or other denaturing agents (used in other procedures). The exogenous acid protease inactivates endogenous nucleases irreversibly and liberates nucleic acids from the biological sample in one step. This procedure may be readily and simply used to isolate nucleic acids from a biological sample for genetic diagnosis and thus is useful in a clinical laboratory.

The following examples are set forth to illustrate various aspects of the present invention, but do not limit in any way its scope as more particularly set forth in the claims.

EXAMPLE 1

Inhibition of Human Serum RNAses at Low pH

A human blood sample was taken from a healthy volunteer. The blood was allowed to stand at room temperature (about 20° C.) to coagulate. The blood clot was removed by low speed centrifugation. The serum obtained was used as the source of human serum RNAse.

Serum RNAse activity was studied by the following procedure. KCl was added to 5 microliters of serum to a final concentration of 50 mM. HCl was added to a final concentration in a range from 20 mM to 97 mM. RNA was added as substrate of RNAse. The volume was adjusted to 10 microliters. The acidity of the solution varied from pH 1.5 to pH 5.0 depending on the amount of HCl included in the solution. The solution was incubated at 37° C. for 20 minutes to allow degradation of the RNA by the serum RNAse.

The amount of RNA remaining was determined by a chemiluminescent labeled-probe hybridization assay as described in Arnold et al., EP 309230. Briefly, the reaction mixture was denatured by heating at 95° C. upon completing the reaction. A solution containing a chemiluminescent labeled probe (complementary to the RNA in the mixture above) was added and the resulting mixture was incubated at 60° C. for 20 minutes. A reagent was added to selectively inactivate the chemiluminescent label of the unhybridized probe and incubated at 60° C. for 4 minutes. After cooling to room temperature, the chemiluminescence of the hybridized probe was measured in relative light units (RLU) using a luminometer.

About 50% of RNA added to the reaction solution was recovered after treatment at pH 4.0. One hundred percent of RNA added was recovered at pH 3.5 or lower. RNAse activity of the serum was significantly reduced at about pH 4.0 or lower, and its enzymatic activity was completely lost at pH 3.5 or lower. These results are illustrated in Table 1.

$MgCl_2$. RNA was added to the solution and the total volume brought up to 10 microliters. The reaction solution was incubated at 37° C. for 20 minutes to digest the RNA with the human leukocyte RNAse. Upon completing the reaction, the amount of RNA remaining was determined by the labeled-probe hybridization assay described in Example 1.

TABLE 1

|  | pH | HCl conc. (mM) | RLU raw | | *RLU net | | **% RLU |
|---|---|---|---|---|---|---|---|
|  |  |  | Non Serum | With 5 µl Serum | Non Serum | With 5 µl Serum | Recovery |
| Test | 1.5 | 97 | 12762 | 15341 | 12042 | 13665 | 113.5 |
|  | 1.5–2 | 86 | 16721 | 15346 | 16001 | 13670 | 85.4 |
|  | 2 | 75 | 13440 | 14701 | 12720 | 13025 | 102.4 |
|  | 2–2.5 | 64 | 11907 | 13911 | 11187 | 12235 | 109.3 |
|  | 3 | 53 | 14198 | 14638 | 13478 | 12962 | 96.2 |
|  | 3.5 | 42 | 15124 | 14814 | 14404 | 13138 | 91.2 |
|  | 4–4.5 | 33 | 16011 | 6698 | 15291 | 5022 | 32.8 |
|  | 5 | 20 | 16317 | 2211 | 15597 | 535 | 3.4 |
| Controls Non RNA | 1.5 | 97 | 720 | 1676 | 0 | 0 | 0 |

*RLU net: The RLUS of reactions without target RNA (background) were 720 RLU and 1676 RLU in Non Serum and With Serum reactions respectively. "RLU net" indicates the raw RLU values minus background RLU values.
**% RLU Recovery: RLU value of With Serum reaction/RLU value of Non Serum reaction × 100

EXAMPLE 2

Human Leukocyte RNAse

The blood of a healthy volunteer was treated with saponin to dissolve erythrocytes. The leukocytes were collected by low speed centrifugation. The leukocytes were then washed with physiological saline and dissolved in a buffer containing Triton X-100. The resulting solution was used as the human leukocyte RNAse solution.

The pH dependency of human leukocyte RNAse was then studied by a procedure similar to that in Example 1. Briefly, the RNAse solution was added to 40 mM potassium acetate pH 4.0 buffer containing 12.25 mM NaCl and 10 mM As a control, 30 ml of Tris-HCl buffer (pH 7.7) was used instead of potassium acetate buffer to prepare the reaction mixture. Human leukocyte RNAse solution, prepared from 5 microliters of blood, was added and a reaction procedure similar to that described above was carried out. In the reaction mixture buffered at pH 7.7, the added RNA was digested to a non-detectable level by the leukocyte RNAse obtained from the 5 microliters of human blood under these conditions. In contrast, about 85% of the original RNA was recovered when human leukocyte RNAse solution from 100 microliters of blood was added to a reaction mixture at pH 4.0. Thus, human leukocyte RNAse activity is substantially reduced at pH 4.0. The results of two sets of tests are shown in Table 2.

TABLE 2

|  |  | pH | Buffering Agent | * Volume of Blood WBC RNase | RLU raw | **RLU net | ***% RLU Recovery |
|---|---|---|---|---|---|---|---|
|  |  |  |  | Test 1 |  |  |  |
| Test |  | 7.7 | 20 mM TrisCl | 0 | 14655 | 14108 | 100 |
|  |  | 7.7 | 20 mM TrisCl | 0.06 | 10885 | 10338 | 73.3 |
|  |  | 7.7 | 20 mM TrisCl | 0.2 | 5403 | 4856 | 34.4 |
|  |  | 7.7 | 20 mM TrisCl | 0.6 | 1466 | 919 | 6.5 |
|  |  | 7.7 | 20 mM TrisCl | 1.7 | 981 | 434 | 3.1 |
|  |  | 7.7 | 20 mM TrisCl | 5 | 1461 | 914 | 6.5 |
| Test |  | 4 | 40 mM K.Acetate | 0 | 11574 | 11000 | 100 |
|  |  | 4 | 40 mM K.Acetate | 0.06 | 11396 | 10822 | 98.4 |
|  |  | 4 | 40 mM K.Acetate | 0.2 | 10797 | 10223 | 92.9 |
|  |  | 4 | 40 mM K.Acetate | 0.6 | 11481 | 10907 | 99.2 |
|  |  | 4 | 40 mM K.Acetate | 1.7 | 10407 | 9833 | 89.4 |
|  |  | 4 | 40 mM K.Acetate | 5 | 11470 | 10896 | 99.1 |
| Controls |  |  |  |  |  |  |  |
|  | Non RNA | 7.7 | 20 mM TrisCl | 0 | 547 | 0 | 0 |
|  | Non RNA | 4 | 40 mM Na.Acetate | 0 | 574 | 0 | 0 |
|  |  |  |  | Test 2 |  |  |  |
| Test |  | 7.7 | 20 mM TrisCl | 0 | 19694 | 19057 | 100 |
|  |  | 7.7 | 20 mM TrisCl | 0.06 | 15407 | 14770 | 77.5 |
|  |  | 7.7 | 20 mM TrisCl | 0.2 | 5986 | 5349 | 28.1 |
|  |  | 7.7 | 20 mM TrisCl | 0.6 | 1040 | 403 | 2.1 |
|  |  | 7.7 | 20 mM TrisCl | 1.7 | 948 | 311 | 1.6 |
|  |  | 7.7 | 20 mM TrisCl | 5 | 694 | 57 | 0.3 |

TABLE 2-continued

|  | pH | Buffering Agent | *Volume of Blood WBC RNase | RLU raw | **RLU net | ***% RLU Recovery |
|---|---|---|---|---|---|---|
| Test | 4 | 40 mM K.Acetate | 0 | 15195 | 14566 | 100 |
|  | 4 | 40 mM K.Acetate | 1.3 | 13429 | 12800 | 87.9 |
|  | 4 | 40 mM K.Acetate | 4 | 14195 | 13566 | 93.1 |
|  | 4 | 40 mM K.Acetate | 11.9 | 14712 | 14083 | 96.7 |
|  | 4 | 40 mM K.Acetate | 35.7 | 13932 | 13303 | 91.3 |
|  | 4 | 40 mM K.Acetate | 107 | 13115 | 12486 | 85.7 |
| Control |  |  |  |  |  |  |
| Non RNA | 7.7 | 20 mM TrisCl | 0 | 637 | 0 | 0 |
| Non RNA | 4 | 40 mM K.Acetate | 0 | 629 | 0 | 0 |

*Volume of blood WBC lysate: Volume of blood from which WBC RNase preparation was obtained.
**RLU net: "RLU net" indicates the RLU values subtracted with the background RLUs from raw values (Background is the RLU value of reactions where Non RNA is present.)
***%RLU Recovery: % of RLU against RLU value of Non WBC lysate reaction

EXAMPLE 3

Recovery of Added RNA

Serum from healthy volunteers was isolated by a conventional procedure. KCl, NaCl and MgCl$_2$ was added to a final concentration of 50 mM, 86 mM, 10 mM and 25 mM, respectively, to 5 microliters serum. The acidity of the solution was adjusted to pH 2.5–1.0 to inactivate RNAses in the mixture. RNA was added as a substrate, and the volume brought up to 10 microliters with water. Pepsin was then added to a final amount of between 2.5 and 200 units. This mixture was incubated at 37° C. for 5 minutes. Upon completion of the reaction, Tris base was added to the reaction mixture to a final concentration of 50 mM, and the volume of the mixture brought up to 20 microliters. This base neutralizes the acidity of the mixture and adjusts the pH to about 7.0. The mixture was incubated at 37° C. for an additional 20 minutes. Upon completing the reaction, RNA remaining in the mixture was denatured by heating at 95° C., and a labelled probe (complementary to the RNA in the above mixture) was added. The mixture was incubated at 60° C. for 20 minutes and assayed for any remaining RNA performed as above.

One hundred percent of the exogenous RNA was recovered under these conditions in the presence of pepsin at 2.5 units or more. This example demonstrates that serum RNAse is irreversibly inactivated by pepsin, and that exogenous RNA in the reaction mixture can be recovered without being affected by serum nucleases. These results are shown in Table 3.

TABLE 3

|  | Pepsin (U/10 µl Reaction) | Serum (µl/10 µl Reaction) | RLU raw | *RLU net | **% RLU Recovery |
|---|---|---|---|---|---|
| Tests | 0 | 5 | 1816 | 69 | 0.1 |
|  | 2.5 | 5 | 85595 | 83848 | 147 |
|  | 5 | 5 | 84773 | 83026 | 145 |
|  | 10 | 5 | 72493 | 70746 | 124 |
|  | 25 | 5 | 92796 | 91049 | 160 |
|  | 50 | 5 | 92204 | 90457 | 158 |
|  | 100 | 5 | 86124 | 84377 | 148 |
|  | 200 | 5 | 80382 | 78635 | 138 |
| Controls |  |  |  |  |  |
| Non RNA. | 0 | 0 | 1747 | 0 | 0 |
| Non Serum | 0 | 0 | 58822 | 57075 | 100 |

*RLU net: The background RLU was 1747. RLU net = RLU raw − 1747
**% RLU Recovery: The total RLU net was 57075. % RLU Recovery = RLU net/57075 × 100

EXAMPLE 4

HCV Test Sample

The procedure of the present invention was evaluated by using a sample serum including hepatitis C virus. The sample serum used was obtained from a hepatitis C infected patient, confirmed to be hepatitis C virus positive by a commercial hepatitis C antibody detection kit.

In order to confirm the recovery of hepatitis C viral RNA without degradation by endogenous serum RNAse, the trace amount of RNA present in such a sample must be amplified after extraction from the sample. In this example, the RNA target is used to form a DNA target by a procedure which amplifies the nucleic acids using reverse transcriptase. The DNA product obtained is then amplified twice by a PCR procedure. Random primers were used in the reverse transcription reaction, and two primers were used in each PCR procedure. This procedure is provided in detail below.

Five microliters of HCV positive serum were taken and 5 microliters HCl buffer (86 mM HCl, 50 mM KCl, 10 mM MgCl$_2$, and 25 mM NaCl) were added. 25 units of pepsin (Macaloid treated) were then added. The mixture was incubated at 37° C. for 15 minutes. The HCV sample was neutralized to pH 7.0 by addition of 5 µl of 172 mM KOH solution. The mixture was heated to 95° C. for 2 minutes, and cooled to room temperature (about 20° C.), 75 µl of reaction premix containing 0.5 microgram (250 pmol) of random primers (TaKaRa, Japan), 13.3 mM Tris-HCl (pH 8.3), 0.7 mM MgCl$_2$, and 0.27 mM each of dATP, dTTP, dGTP, and dCTP (Pharmacia) were then added and the total volume brought up to 90 microliters. The mixture was heated to 65° C. for 5 minutes and cooled to room temperature. 1 µl containing 200 units/µl of MMLV reverse transcriptase (BRL) was added to the reaction mixture, and the mixture incubated at 37° C. for 30 minutes. PCR reactions were performed in accordance with the conditions specified in Mullis, U.S. Pat. No. 4,683,195. Briefly, upon completing the reverse transcription reaction, 100 pmol of two primers was added which correspond to the NS5 region of HCV. 2.5 units of Taq DNA polymerase were added and the total volume brought up to 100 µl. The reaction products were denatured by heating for 2 minutes at 92° C. A cycle of heating and cooling was repeated 40 times. (Each cycle includes heating at 92° C. for 1.5 minutes, heating at 53° C. for 1.5 minutes, and heating at 70° C. for 2 minutes). The resulting mixture was then incubated at 70° C. for 9 minutes.

A 10 microliter aliquot of the mixture was then mixed with a secondary primer set designed to hybridize in a location within the primary primer set used in the primary PCR reaction. (The actual primers used in these examples are not essential in this invention.) The volume of the mixture was brought up to 100 microliters, and the secondary PCR reaction performed under the same conditions used in the primary PCR reaction. (Specifically, 10 mM Tris-HCl, pH 8.3, 100 pmol primers, 1.5 mM $MgCl_2$, 50 mM KCl, 0.2 mM each dNTP, and 2.5 units of Taq polymerase were used.)

The nucleic acids obtained from these amplifications were denatured by heating at 95° C. for 5 minutes. 90 µl labelled probe was added to assay for nucleic acids using the method described in Example 1. The results are summarized in Table 4.

TABLE 4

| Serum Specimen | RLU Observed |
|---|---|
| Healthy | 686 |
| Patient PI | 10027 |
| Patient POM | 6553 |
| Patient POT | 5422 |

These data indicate that the strength of the signals of an HCV positive serum is 8 to 15 times greater than that of a healthy serum. Thus, HCV RNA was liberated by the procedure without being affected by endogenous RNAses. This example also demonstrates that the RNA isolated by the methods of this invention can be used as a substrate for enzymatic reactions without any other purification or isolation process. Accordingly, it is expected that the methods of the present invention can be widely used by themselves, or in combination with other amplification procedures in order to detect specific nucleic acids in diagnostic tests.

EXAMPLE 5

HCV Test Sample, Non-PCR Amplification

The following is another protocol for detection of nucleic acid in an HCV sample. 5 µl of pepsin solution in buffer (KCl/HCl or Glycine/HCl) is placed into appropriate tubes (pepsin was obtained from Sigma). The pepsin solution for KCl/HCl buffer contains 25 U pepsin in 100 mM KCl-172 mM HCl; and for Glycine/HCl buffer contains 25 U pepsin in 400 mM Glycine-400 mM HCl.

5 µl of serum specimen (healthy or HCV infected patient) was added to these tubes, and incubated at 37° C. for 15 minutes.

10 µl of neutralization solution was added (neutralization solution for KCl/HCl buffer is 172 mM KOH-128 mM KCl; and for Glycine/HCl buffer was 200 mM KOH). The sample was then amplified essentially as described by Kacian and Fultz, NUCLEIC ACID SEQUENCE AMPLIFICATION METHODS UTILIZING A TRANSCRIPTION COMPLEX, PCT/US90/03907. This mixture was incubated at 37° C. for 4 hours, and 10 µl of amplified samples subject to HPA using AE-CP-6278 probe (NS5 region). The results are shown in Table 5.

TABLE 5

| | RLU Observed | |
|---|---|---|
| Serum Specimen | KCl/HCl Buffer | Glycine/HCl Buffer |
| Healthy | 3541 | 1127 |
| Patient PKB | 15165 | 1421 |

TABLE 5-continued

| | RLU Observed | |
|---|---|---|
| Serum Specimen | KCl/HCl Buffer | Glycine/HCl Buffer |
| Patient PN-1 | 101146 | 82361 |
| Patient PT-1 | 166160 | 1051277 |
| Patient PH-1 | 802740 | 907997 |
| Patient PY-2 | 1143597 | 1126462 |
| Patient P- 7 | 1143699 | 1147653 |
| Patient P-37 | 407889 | 471565 |
| Patient P-27 | 1089869 | 1113446 |
| Patient P-32 | 512470 | 516870 |
| Patient P-37 | 314846 | 579284 |
| Patient P-38 | 948738 | 756643 |

These results show that HCV can be detected using a non-PCR amplification system in conjunction with the present invention.

EXAMPLE 6

Procedure for Purifying Pepsin with Macaloid

The following is a procedure for preparing pepsin free of potentially harmful enzyme activities.

A. Preparation of stock solution of Macaloid suspension (16 mg/ml): (This procedure is the same as that described in Molecular Cloning 1st Edition (Maniatis et al., 1982, p452)).
1. Weigh 0.25 g of Macaloid.
2. Suspend 0.25 g of Macaloid in 25 ml of 50 mM Tris-HCl pH 7.5.
3. Boil the suspension at 100° C. for 5 minutes with constant agitation.
4. Centrifuge the Macaloid suspension at 2500×g at 4° C.
5. Discard the supernatant.
6. Re-suspend the pellet in 20 ml of 50 mM Tris-HCl pH 7.5.
7. Centrifuge the Macaloid suspension at 2500×g at 4° C.
8. Repeat the procedure 5 through 7 (washing procedure) 4 more times.
9. Re-suspend the sticky pellet in 15 ml of 50 mM Tris-HCl pH 7.5.
10. Store the Macaloid suspension at 4° C. or −20° C.

B. Preparation of working Macaloid suspension for adsorption of contaminated RNAse in pepsin:

Pepsin is readily inactivated at neutral pH. Therefore the buffer suspending Macaloid should be substituted with buffer of acidic pH to use in pepsin preparation.
1. Place Macaloid suspension in 50 mM Tris-HCl into EPPENDORF tube.
2. Centrifuge the Macaloid suspension at 5000 rpm in microfuge (5 minutes).
3. Discard the supernatant.
4. Add 150 mM NaCl-10 mM sodium acetate buffer pH 5.2.
5. Stand the Macaloid suspension at 4° C. for several hours.
6. Centrifuge the tube at 5000 rpm in microfuge (5 minutes).
7. Discard the supernatant.
8. Repeat procedure 4 through 7 until the pH of Macaloid suspension is below 5.5. (Typically this takes four or five repeats of buffer substitution.)
9. Re-suspend the Macaloid in 150 mM NaCl-10 mM sodium acetate buffer pH 5.2 (same volume as starting volume).

C. Adsorption of contaminated RNAse in pepsin to Macaloid:

1. Dissolve pepsin (Sigma Cat#6887) in 10 mM HCl-50% Glycerol to 345 U/µl.
2. Place 150 µl of pepsin in EPPENDORF tube.
3. Add 50 µl of Macaloid suspension in 150 mM NaCl-10 mM sodium acetate buffer pH 5.2 and mix.
4. Keep the tube in ice-water for 2 hours.
5. Centrifuge the tube at 7500 rpm in microfuge for 10 minutes at 4° C.
6. Transfer 150 µl of supernatant to another tube. (The pH of the supernatant is around 4.5.)
7. Add another 50 µl of Macaloid suspension in step 3 and mix.
8. Keep the tube at 4° C. for 15 minutes.
9. Centrifuge the tube at 7500 rpm in microfuge for 10 minutes at 4° C.
10. Transfer 150 µl of supernatant to another tube. (The pH of the supernatant is around 4.5.)
11. Add 50 µl of Macaloid suspension in step 3 and mix.
12. Keep the tube at 4° C. for 15 minutes.
13. Centrifuge the tube at 7500 rpm in microfuge (10 minutes).
14. Take the supernatant into another tube and keep it at −20° C. (The pH of the supernatant is 4.5–5.0 (close to 4.5))

D. Assay for pepsin activity:

Pepsin activity after adsorption procedure to Macaloid was tested by standard procedure after each adsorption step. The results are shown in Table 6.

TABLE 6

| Pepsin (Unit equivalent/ Rxn) | A 520 nm | | | |
| --- | --- | --- | --- | --- |
| | Original soln | 1st Adsorption | 2nd Adsorption | 3rd Adsorption |
| 0 | 0.12 | 0.12 | 0.12 | 0.12 |
| 10 | 0.32 | 0.36 | 0.46 | 0.44 |
| 40 | 1.37 | 1.03 | 1.02 | 1.20 |
| 70 | 1.91 | 1.78 | 1.69 | 1.77 |
| 100 | 2.23 | 1.74 | 2.26 | 2.16 |

The pepsin activity after adsorption is calibrated using the standard curve drawn from the original pepsin solution.

This data shows that pepsin activity was not affected by Macaloid adsorption procedure.

E. Assay for contaminating RNAse activity in pepsin:

Contaminating RNAse activities in pepsin were measured by monitoring loss of ability of an acridinium ester-labelled DNA probe to hybridize to an RNA substrate. The RNA used was an in vitro synthesized transcript of sequences found in a portion of the ribosomal RNA of *Chlamydia trachomatis*. Contaminating RNAse activities in both original pepsin solution (non-adsorption) and pepsin preparation after the third adsorption were tested.

The reactions were set up so that each reaction tube contained the amount of RNA transcript which, when annealed with the DNA probe, produced 40,000 relative light units (RLU) signal in the absence of RNAse, 50 mM Tris-HCl (pH 7.5), 10 mM $MgCl_2$, 25 mM NaCl, and 2% Glycerol. 0 U, 345 U or 690 Units equivalent of a pepsin preparation were added. The total volume was 20 µl. Negligible or non-detectable amounts of RNAse activity was detectable after Macaloid treatment of the pepsin.

The present disclosure and patent applications cited in this specification show the technical levels of those skilled in the art. It will be apparent to those skilled in the art, that various changes, modifications, and variations may be made without departing from the spirit and scope of the invention as defined by the present claims.

Other embodiments are within the following claims.

What is claimed is:

1. A kit for making available in solution or suspension a nucleic acid present in a biological sample and for further processing said nucleic acid, said kit consisting essentially of the following components in separate compartments:

an acid able to reduce the pH of said sample to a pH at or below pH 4.0;

an acid protease able to digest cellular materials in said biological sample to release said nucleic acid in said biological sample and to inactivate endogenous nucleases which may be present therein;

a base able to raise the pH of said biological sample to a pH at which said protease is not active; and a labeled probe in a form suitable for use in a hybridization assay.

2. The kit of claim 1, wherein said acid protease is pepsin.

3. The kit of claim 1 further consisting essentially of a detergent in a separate compartment.

4. The kit of claim 1, wherein said probe is a DNA probe.

5. The kit of claim 3, wherein said probe is a DNA probe.

* * * * *